US005462872A

United States Patent [19]

Jonak et al.

[11] Patent Number: 5,462,872
[45] Date of Patent: Oct. 31, 1995

[54] HUMAN LYMPHOID CELLS EXPRESSING HUMAN IMMUNODEFICIENCY VIRUS ENVELOPE PROTEIN GP160

[75] Inventors: Zdenka L. Jonak, Devon; Christine Debouck, Wayne, both of Pa.; Robert Clark, Woodstown, N.J.; Stephen Trulli, Havertown, Pa.

[73] Assignee: SmithKline Beecham Corporation, Philadelphia, Pa.

[21] Appl. No.: 134,128

[22] Filed: Oct. 8, 1993

Related U.S. Application Data

[63] Continuation of Ser. No. 906,613, Jun. 30, 1992, which is a continuation of Ser. No. 587,011, Sep. 24, 1990, abandoned.

[51] Int. Cl.$^6$ ............................................................ C12N 5/22
[52] U.S. Cl. ................. 435/240.2; 435/7.2; 435/69.1; 435/69.3; 435/70.3; 435/172.1; 435/172.3; 435/240.1; 435/974
[58] Field of Search ............................. 435/7.2, 69.3, 435/70.3, 172.3, 240.1, 974, 69.1, 172.1, 240.2; 530/350, 395

[56] References Cited

U.S. PATENT DOCUMENTS 4,910,132  3/1990  Knight et al. ............................. 435/5

OTHER PUBLICATIONS

Klein et al., *Proc. Nat. Acad. Sci.*, 71:3283–3286 (1974), "Continuous Lymphoid Cell Lines With Characteristics of B Cells (Bone–Marrow–Derived), Lacking the Epstein–Barr Virus Genome and Derived from Three Human Lymphomas".

Ratner, et al., *Nature*, 313:277–284 (1985).

Sodroski, et al., *Nature*, 321:412–417 (1986).

Schnittman, et al., *Journal of Immunology*, 141:4181–4186 (1988).

Hay, et al., Eds., "American Type Culture Collection Catalogue of Cell Lines and Hybridomas", 6th Edition, p. 53 (1988).

Sodroski et al: Role of the HTLV–III/LAV envelope in syncytium formation & cytopathicity; Nature, vol. 322 pp. 470–474, 1986.

*Primary Examiner*—Christine M. Nucker
*Assistant Examiner*—Jeffrey Stucker
*Attorney, Agent, or Firm*—Jeffrey A. Sutton; Herbert H. Jervis; Edward T. Lentz

[57] ABSTRACT

The present invention provides mammalian cells modified to stably express at least the entire human immunodeficiency virus-1 envelope protein gp160. The invention provides a vaccine comprising the cells of the invention. The invention also provides methods for screening compounds for their ability to inhibit formation of syncytia between cells that express HIV-1 gp160 and cells that express CD4 comprising mixing cells of invention, cells that express CD4 on their surfaces, and a test compound for a length of time sufficient for syncytia to form; and then determining the amount of syncytia formation.

4 Claims, 3 Drawing Sheets

Figure 1a

```
        (*)                 V start rev - exon 1
  1   CCTTAGGCAT CTCCTATGGC AGGAAGAAGC GGAGACAGCG ACGAAGACCT
                                      end rev - exon 1 V
 51   CCTCAAGGCA GTCAGACTCA TCAAGTTTCT CTATCAAAGC AGTAAGTAGT

101   ACATGTAATG CAACCTATAC AAATAGCAAT AGTAGCATTA GTAGTAGCAA

151   TAATAATAGC AATAGTTGTG TGGTCCATAG TAATCATAGA ATATAGGAAA

201   ATATTAAGAC AAAGAAAAAT AGACAGGTTA ATTGATAGAC TAATAGAAAG
                          V start env open reading frame (gp120)
251   AGCAGAAGAC AGTGGCAATG AGAGTGAAGG AGAAATATCA GCACTTGTGG

301   AGATGGGGGT GGAGATGGGG CACCATGCTC CTTGGGATGT TGATGATCTG

351   TAGTGCTACA GAAAAATTGT GGGTCACAGT CTATTATGGG GTACCTGTGT

401   GGAAGGAAGC AACCACCACT CTATTTTGTG CATCAGATGC TAAAGCATAT

451   GATACAGAGG TACATAATGT TTGGGCCACA CATGCCTGTG TACCCACAGA

501   CCCCAACCCA CAAGAAGTAG TATTGGTAAA TGTGACAGAA AATTTTAACA

551   TGTGGAAAAA TGACATGGTA GAACAGATGC ATGAGGATAT AATCAGTTTA

601   TGGGATCAAA GCCTAAAGCC ATGTGTAAAA TTAACCCCAC TCTGTGTTAG

651   TTTAAAGTGC ACTGATTTGA AGAATGATAC TAATACCAAT AGTAGTAGCG

701   GGAGAATGAT AATGGAGAAA GGAGAGATAA AAAACTGCTC TTTCAATATC

751   AGCACAAGCA TAAGAGGTAA GGTGCAGAAA GAATATGCAT TTTTTTATAA

801   ACTTGATATA ATACCAATAG ATAATGATAC TACCAGCTAT ACGTTGACAA

851   GTTGTAACAC CTCAGTCATT ACACAGGCCT GTCCAAAGGT ATCCTTTGAG

901   CCAATTCCCA TACATTATTG TGCCCGGGCT GGTTTTGCGA TTCTAAAATG

951   TAATAATAAG ACGTTCAATG GAACAGGACC ATGTACAAAT GTCAGCACAG

1001  TACAATGTAC ACATGGAATT AGGCCAGTAG TATCAACTCA ACTGCTGTTA

1051  AATGGCAGTC TGGCAGAAGA AGAGGTAGTA ATTAGATCTG CCAATTTCAC

1101  AGACAATGCT AAAACCATAA TAGTACAGCT GAACCAATCT GTAGAAATTA

1151  ATTGTACAAG ACCCAACAAC AATACAAGAA AAGTATCCG TATCCAGAGA

1201  GGACCAGGGA GAGCATTTGT TACAATAGGA AAAATAGGAA ATATGAGACA

1251  AGCACATTGT AACATTAGTA GAGCAAAATG GAATAACACT TTAAAACAGA

1301  TAGATAGCAA ATTAAGAGAA CAATTTGGAA ATAATAAAAC AATAATCTTT
```

Figure 1b

```
1351  AAGCAGTCCT CAGGAGGGGA CCCAGAAATT GTAACGCACA GTTTTAATTG

1401  TGGAGGGGAA TTTTTCTACT GTAATTCAAC ACAACTGTTT AATAGTACTT

1451  GGTTTAATAG TACTTGGAGT ACTAAAGGGT CAAATAACAC TGAAGGAAGT

1501  GACACAATCA CCCTCCCATG CAGAATAAAA CAAATTATAA ACATGTGGCA

1551  GGAAGTAGGA AAAGCAATGT ATGCCCCTCC CATCAGTGGA CAAATTAGAT

1601  GTTCATCAAA TATTACAGGG CTGCTATTAA CAAGAGATGG TGGTAATAGC

1651  AACAATGAGT CCGAGATCTT CAGACCTGGA GGAGGAGATA TGAGGGACAA

1701  TTGGAGAAGT GAATTATATA AATATAAAGT AGTAAAAATT GAACCATTAG
                                                          end gp120
1751  GAGTAGCACC CACCAAGGCA AAGAGAAGAG TGGTGCAGAG AGAAAAAAGA
      V start gp41
1801  GCAGTGGGAA TAGGAGCTTT GTTCCTTGGG TTCTTGGGAG CAGCAGGAAG

1851  CACTATGGGC GCAGCGTCAA TGACGCTGAC GGTACAGGCC AGACAATTAT

1901  TGTCTGGTAT AGTGCAGCAG CAGAACAATT TGCTGAGGGC TATTGAGGCG

1951  CAACAGCATC TGTTGCAACT CACAGTCTGG GGCATCAAGC AGCTCCAGGC

2001  AAGAATCCTG GCTGTGGAAA GATACCTAAA GGATCAACAG CTCCTGGGGA

2051  TTTGGGGTTG CTCTGGAAAA CTCATTTGCA CCACTGCTGT GCCTTGGAAT

2101  GCTAGTTGGA GTAATAAATC TCTGGAACAG ATTTGGAATA ACATGACCTG

2151  GATGGAGTGG GACAGAGAAA TTAACAATTA CACAAGCTTA ATACACTCCT

2201  TAATTGAAGA ATCGCAAAAC CAGCAAGAAA AGAATGAACA AGAATTATTG

2251  GAATTAGATA AATGGGCAAG TTTGTGGAAT TGGTTTAACA TAACAAATTG

2301  GCTGTGGTAT ATAAAATTAT TCATAATGAT AGTAGGAGGC TTGGTAGGTT

2351  TAAGAATAGT TTTTGCTGTA CTTTCTGTAG TGAATAGAGT TAGGCAGGGA
                                   V start rev - exon 2
2401  TATTCACCAT TATCGTTTCA GACCCACCTC CCAATCCCGA GGGGACCCGA

2451  CAGGCCCGAA GGAATAGAAG AAGAAGGTGG AGAGAGAGAC AGAGACAGAT

2501  CCATTCGATT AGTGAACGGA TCCTTAGCAC TTATCTGGGA CGATCTGCGG

2551  AGCCTGTGCC TCTTCAGCTA CCACCGCTTG AGAGACTTAC TCTTGATTGT

2601  AACGAGGATT GTGGAACTTC TGGGACGCAG GGGGTGGGAA GCCCTCAAAT
                                                     end rev - exon 2 V
2651  ATTGGTGGAA TCTCCTACAG TATTGGAGTC AGGAGCTAAA GAATAGTGCT
```

Figure 1c

```
2701  GTTAGCTTGC TCAATGCCAC AGCTATAGCA GTAGCTGAGG GGACAGATAG

2751  GGTTATAGAA GTAGTACAAG GAGCTTATAG AGCTATTCGC CACATACCTA
                                        end gp41 V
2801  GAAGAATAAG ACAGGGCTTG GAAAGGATTT TGCTATAAGA TGGGTGGCAA 2851  GTGGTCAAAA AGTAGTGTGG TTGGATGGCC TGCTGTAAGG GAAAGAATGA
                                                          (*)
2901  GACGAGCTGA GCCAGCAGCA GATGGGGTGG GAGCAGCATC TCGAG
```

HUMAN LYMPHOID CELLS EXPRESSING HUMAN IMMUNODEFICIENCY VIRUS ENVELOPE PROTEIN GP160

This is a continuation of application Ser. No. 07/906,613, filed Jun. 30, 1992, which is a continuation of Ser. No. 07/587,011 filed on Sep. 24, 1990 now abandoned.

FIELD OF THE INVENTION

The present invention relates to the field of cells transfected by recombinant DNA techniques to express heterologous proteins. More particularly, the present invention relates to cells transfected by recombinant DNA techniques to express viral proteins, and their use as vaccines for prevention of disease, and in assay systems in the drug discovery process.

BACKGROUND OF THE INVENTION

HIV-1 is the etiological agent of acquired human immune deficiency syndrome (AIDS) and related disorders. HIV-1 is an RNA virus of the Retroviridae family and exhibits the same 5'LTR-gag-pol-env-LTR3' organization as all retroviruses. In addition, it comprises a handful of genes with regulatory or unknown function, in particular the tat and rev genes. The env gene encodes the viral envelope glycoprotein that is first translated as a 160-kilodalton (kDa) precursor (gp160), which is subsequently cleaved by a cellular protease to yield the external 120-kDa envelope glycoprotein (gp120) and the transmembrane 41-kDa envelope glycoprotein (gp41). Gp120 and gp41 remain associated and are displayed on the viral particles as well as on the surface of HIV-infected cells. Gp120 is directly responsible for binding to the CD4 receptor present on the surface of helper T-lymphocytes, macrophages and other target cells. After gp120 binds to CD4, gp41 mediates the fusion event responsible for virus entry.

Infection begins as gp120 on the viral particle binds tightly to the CD4 receptor on the surface of T4 lymphocytes or other target cells. The virus then merges with the target cell and reverse transcribes its RNA genome into double-stranded DNA. The viral DNA becomes incorporated into the genetic material in the cell's nucleus and directs the production of new viral RNA and viral proteins, which combine to form new virus particles. These particles bud from the target cell membrane and infect other cells.

Destruction of T4 lymphocytes, which are critical to immune defense, is the major cause of the progressive immune dysfunction that is the hallmark of HIV infection. The loss of targetcells seriously impairs the body's ability to fight most invaders, but it has a particularly severe impact on the defenses against viruses, fungi, parasites and certain bacteria, including mycobacteria.

HIV-1 is known to kill the cells it infects by replicating, budding from them and damaging the cell membrane. HIV-1 might also kill target cells indirectly, by means of the viral protein, gp120, that is displayed on an infected cell's surface. The CD4 receptor on T cells has a strong affinity for gp120, and healthy T4 cells and cells expressing CD4 receptor can bind to gp120 and fuse with infected cells. In addition to the CD4-gp120 interaction, other receptors may also play a role in the fusion process. The end result, called a syncytium, cannot survive, and all the once healthy cells it contains are destroyed along with the infected cell. HIV-1 can also elicit normal cellular immune defenses against infected cells. With or without the help of antibodies, cytotoxic defensive cells can destroy an infected cell that displays viral proteins on its surface. Finally, free gp120 may circulate in the blood of individuals infected with HIV-1. The free protein may bind to the CD4 receptor of uninfected cells, making them appear to be infected and evoking an immune response.

Infection with HIV-1 is almost always fatal, and at present there are no cures for HIV-1 infection. Effective vaccines for prevention of HIV-1 infection are not yet available. Because of the danger of reversion or infection, conventional live attenuated virus or killed whole virus cannot be used as vaccines. Also most subunit vaccine approaches have not been successful at preventing HIV infection to date. In addition, treatments for HIV-1 infection, while prolonging the life of infected persons to some extent, have serious side effects. There is thus a great need for effective treatments and vaccines to combat this lethal infection.

Vaccination is an effective form of disease prevention and has proven successful against several types of viral infection. Determining ways to present HIV-1 antigens to the human immune system in order to evoke protective humoral and cellular immunity, is a difficult task. At the present time most attempts to generate an effective HIV vaccine have been unsuccessful. In AIDS patients, free virus is present in low levels only. Transmission of HIV-1 is enhanced by cell-to-cell interaction via fusion and syncytia formation. Hence, antibodies generated against free virus or viral subunits are generally ineffective in eliminating virus-infected cells.

Vaccines exploit the body's ability to "remember" an antigen. After first encounters with a given antigen the immune system generates cells that retain an immunological memory of the antigen for an individual's lifetime. Consequently, subsequent exposure to the antigen results in elimination or inactivation of the pathogen. The immune system deals with pathogens in two ways: by humoral and by cell-mediated responses. In the humoral response lymphocytes generate specific antibodies that bind to the antigen thus inactivating the pathogen. The cell-mediated response involves cytotoxic lymphocytes that specifically attack and destroy infected cells.

Vaccine development with HIV-1 virus presents problems because the virus infects some of the same cells the vaccine needs to activate in the immune system (i.e., T4 lymphocytes). Therefore it would be advantageous for the vaccine to inactivate the HIV before impairment of the immune system occurs. A particularly suitable type of HIV vaccine would generate an anti-HIV immune response which will recognize innumerable HIV variants and will extend its activity to HIV-positive individuals who are at the beginning of their infection.

It is accordingly an object of the invention to provide vaccines for use in the prevention and treatment of HIV-1 infection. It is also an object of the invention to provide methods for screening compounds that inhibit the deleterious syncytia formation for use as treatments for HIV-1 infection.

Sodroski, J. et al. (1986) Nature 322: 470–474 discloses T4+Jurkat-tat-III cells (a T4+Burkitt's lymphoma cell line that expresses the HIV-1 tat gene product) transfected with a plasmid designed to express both the rev and env gene products. These cells transiently expressed HIV-1 gp160, and were used in a syncytia formation assay in studies on the basis of the specific cytotoxicity of the AIDS virus. Although the cells expressed HIV-1 gp160, transient expression of the envelope protein is inconvenient and time-consuming for use in syncytium formation assays, since new cells would have to be transfected at frequent intervals.

Palker, T.J. et al (1987) Proc. Natl. Acad. Sci. USA 84: 2479–2483 also discloses a syncytia formation assay. The assay was used for the study of antibodies specific for HIV-1 proteins.

SUMMARY OF THE INVENTION

The present invention provides mammalian cells modified to stably express a heterologous protein comprising at least the entire HIV-1 envelope protein gp160. The invention also provides vaccines for prevention of HIV-1 infection comprising the cells of the invention. The invention further provides assays for the determination of syncytia formation for screening compounds for their ability to inhibit syncytia formation. This invention is more particularly pointed out in the appended claims and is described in its preferred embodiments in the following description.

BRIEF DESCRIPTION OF THE FIGURE

FIGS. 1A–1C shows the nucleotide sequence of the MstII-XhoI restriction endolucease fragment from BH10 carrying the full-length gp160 envelope gene and the two intact exons of the rev regulatory protein.

DETAILED DESCRIPTION OF THE INVENTION

The present invention provides mammalian cells transfected to express HIV-1 gp160 on their surfaces. The cells are useful in assays to screen for inhibitors of syncytia formation with cells expressing CD4 or other receptors. The cells are also expected to be useful as a vaccine for prevention or inhibition of HIV-1 infection.

Mammalian cells are stably transfected with DNA coding for HIV-1 gp160 which DNA is preferably contained within a plasmid. As used herein, the term "stably transfected", "stably expressed" and similar terms, refer to incorporation of heterologous DNA into a cell where it is expressed for at least the remainder of the life time of the cell and is preferably expressed by future generations of cells derived from the originally transfected cell. Stable transfection of a cell may be distinguished from transient expression of heterologous DNA by a cell by the length of time the recipient cell expresses the heterologous DNA. With transient expression, the cell generally expresses the heterologous protein for a few days or weeks until the vector containing the heterologous DNA is lost from the cell. With stable transfection, the heterologous DNA is expressed for longer periods of time and is passed to later generations of the cells.

The cells of the invention are preferably mammalian cells such as human lymphoid cells, CD4 negative lymphoid cells, and B cells. Preferred lymphoid cells include human Burkitt's lymphoma cell lines such as BJAB, Namalwa, Raji, Daudi, Ramos, EB1 and EB2. A preferred Burkitt's lymphoma cell lines is BJAB. Preferred B cells include early B cell lines such as REH, and immortalized B cells.

BJAB is a human Burkitt's lymphoma cell line, originally described in Klein, G. et al. (1974) Proc. Natl. Acad. Sci. USA 71: 3283. BJAB cells are used in a preferred embodiment of the invention. Phenotypically, with respect to the B-cell differentiation cascade, the BJAB cell line represents an early B-cell type. BJAB cells express B1 and B4 cell surface markers. BJAB cells are preferably cultured in suspension or semi-attached culture in TY medium (Gibco, Grand Island, N.Y.) with 13% calf serum using standard suspension cell culture procedures. Other media suitable for the culture of B JAB cells include DMEM-HG medium (Gibco, Grand Island, N.Y.) and RPMI-1640 (Gibco).

DNA Coding for at least the entire HIV-1 gp160 gene may be obtained using standard techniques such as those in Sambrook et al. *Molecular Cloning, A Laboratory Manual (second edition)* Cold Spring Harbor Laboratories, Cold Spring Harbor, N.Y., 11724 from HIV-1 isolated from cells of infected persons, or from virus obtained from the National Institutes of Health AIDS Research and Reference Program. The DNA fragment coding for HIV-1 gp160 preferably includes the entire coding sequence for gp160, more preferably the sequence the entire coding sequence for gp160 and at least one rev exon.

In a preferred embodiment of the invention, D N A coding for HIV-1 gp160 was obtained from the BH10 HIV-1 isolate described in Shaw et al. (1984) science 226: 1165–1171. The HIV-1 gp160 coding sequence may be isolated on an MstII-XhoI 2945 base pair (bp) restriction endonuclease fragment. This restriction endonuclease fragment carries the intact HIV-1 gp160 env gene as well as the two intact rev exons (coordinates 5535 to 8480, according to the numbering of Ratner et al. (1985) Nature 313: 277). Other restriction fragments may be used, provided at least the entire coding sequence for gp160 is contained within the fragment.

The DNA coding for HIV-1 gp160 may then be inserted into an expression vector, preferably a plasmid expression vector. The expression vector is selected to be compatible with the particular mammalian cell type to be transfected. Preferably a low copy number plasmid is used.

In a preferred embodiment of the invention, DNA coding for HIV-1 gp160, a heterologous protein, is inserted into the expression vector CLDN. After ligation to XbaI linkers and digestion with XbaI, this env carrying fragment was inserted downstream of the cytomegalovirus (CMV) immediate early (IE) promoter in the CLDN expression vector. The CLDN expression vector is derived from the RLDN expression vector which contains the Rous sarcoma virus (RSV) long terminal repeat promoter followed by several cloning sites and the bovine growth hormone polyadenylation site. Both RLDN and CLDN vectors also carry the dehydrofolate reductase (DHFR) and neomycin phosphotransferase gene expression cassettes for plasmid integration, selection and amplification. In CLDN, the RSV promoter has been replaced by the strong and constitutive cytomegalovirus (CMV) immediate early (IE) promoter isolated on an SpeI-SacI restriction endonuclease fragment from the CDM8 vector described by Seed (1987) Nature 329: 840–842.

HIV-1 gp160/rev can be expressed in other mammalian expression Systems, including vectors such as pMSG (Lee et al., (1981) Nature 294: 228); pSVL (Sprague et al. (1983) J. Virology 45: 773); pMT2 (Kaufman et al. (1989) Mol. Cell. Biol. 9: 946); BPV-1 based vectors (DiMaio (1987) in: The papovaviridiae: The papillomaviruses (eds. N.P. Salzman and P.M. Howley), vol. 2, p. 293, Plenum Publishing, New York, N.Y.); and pHEBo (Sugden et al. (1985) Mol. Cell. Biol. 5: 410–413) with other constitutive or regulated promoters such as viral promoters (e.g. retroviral long terminal repeats (MMTV, MuLV), SV40 promoters (early, and late), adenovirus promoters (late), herpes virus promoters (TK), vaccinia virus promoters, hepatitis B virus promoters (precore)), or cellular promoters (e.g. rat β-actin promoter, rat insulin I promoter, rat amylass promoter, human insulin promoter, rat chymotrypsin promoter, mouse metallothionein promoter). The expression vectors can carry selection/amplification markers other than neo/DHFR, e.g. xgprt (xanthine-guanine phosphoribosyltransferase), hygromycin-resistance, hisD. Other polyadenylation signals can be used at the end of the expression cassette, such as the SV40 polyadenylation signal, or herpes simplex virus polyadenylation site.

After preparation of the vector DNA expressing HIV-1 gp160, it is inserted into mammalian recipient or host cells, preferably by transfection. Electroporation is a preferred method of transfection of the cells. BJAB cells are preferably transfected with the gp160-containing expression vector by electroporation. BJAB cells were refractory to transfection using calcium phosphate precipitation. However, other standard techniques for transfection of cells such as DEAE-dextran transfection and lipofection may be suitable for transfection of the cells.

Cells expressing HIV-1 gp160 are then selected using methods designed to detect the selection marker carried on the expression vector. In a preferred embodiment of the invention, the expression vector contains the gene for neomycin resistance and cells are selected by growing the transfected cells in medium containing neomycin. Cells that grow in the medium are neomycin resistant, signaling that they have been transfected with the plasmid containing the selection marker and the gene for HIV-1 gp160.

Identification of cells expressing gp160 may be done using assays designed to detect gp160, or gp120 and gp41, the subunits of gp160. Suitable assays include immunochemical assays employing antibodies to gp120, or gp41, Western blot assay, and syncytia formation assays.

Preferred clones expressing gp160 are TF228.1 and TF228.2. Clone TF228.1.16 produces approximately 0.1–0.3 picograms per cell of gp120 (based on Western blot analysis in which a known amount of pure gp120 expressed in Drosophila was titrated). Six additional clones (TF243A-1 through -6) also stably express HIV-1 gp160.

gp160 is stably expressed on the cell surface of the transfected BJAB cells and appears to be expressed on the cell surface in a processed and functional form, i.e. as gp41 and gp120. gp160 expressed on the surface of transfected BJAB cells is capable of forming syncytia with human lymphoid cells and other cell lines of CD4+ phenotype. Since expression of gp160 is stable, the cells of the invention can be conveniently used in syncytia formation assays, as described herein, overcoming the need for transfection of new cells at frequent intervals. Additionally, stable expression of functional gp160 allows the cells of the invention to be used as vaccines. Cell lines that stably express gp160 will express the protein consistently without loss of expression or significant variation in the concentration of gp160. For production of vaccines it is important that large quantities can be obtained, with stable expression of gp160, so the efficacy of the product will not have to be repeatedly tested.

The cells of the invention are useful in studies on the mechanism of interaction(s) between the gp160 molecule (gp120 and gp41) with the CD4 receptor and other receptor(s) expressed on different cell types (e.g. monocytes, macrophages, cells of central nervous system, EBV infected cells). Additionally, the cells of the invention will provide a unique tool in basic understanding of the cell-to-cell interactions and in exploring the effect(s) of gp120 and gp41 and their role in immune mechanism and response.

The cells of the invention are also useful in methods for testing of compounds for their ability to inhibit formation of syncytia between cells expressing viral gp160 on their surfaces and cells expressing CD4 on their surfaces. One of the effects of HIV-1 infection is the formation of syncytia. Infected CD4+ cells that express HIV-1 envelope protein (gp120 and gp41) on their surfaces bind other CD4+ cells leading to giant cells containing the nuclei of many cells. The death of cells within syncytia is rapid in the in vitro assay system. Cell death, measured by lack of thymidine uptake, occurs within a few hours of syncytia formation. Compounds that can inhibit formation of syncytia by binding to CD4 or the HIV-1 envelope proteins or by any other mechanism such as inhibition of fusion would be useful in the treatment of HIV-1 infection and possibly as preventive therapy.

The syncytia formation assay of the invention is performed by mixing together the cells of the invention and cells expressing CD4 on their surfaces and then adding a test compound. The cells are left to incubate with the test compound for a predetermined length of time and then examined, usually with the aid of a microscope, for the formation of syncytia. Other methods such as measuring thymidine uptake to determine cell death through syncytia formation are also suitable for evaluating the test compound's ability to inhibit syncytia formation. Additional suitable methods for determining syncytia formation include dyes, radioactive compounds, image analysis, uptake of dyes, and enzymatic activity. For example, the cells of the invention and cells expressing CD4 on their surfaces may be labeled with dyes having different absorption/emission characteristics. When syncytia formation occurs the contents of the cells will mix together and the resulting syncytia will contain a mixture of both dyes which will absorb at a different wavelength than the dye in either cell type separately. Absorption may be measured by conventional techniques such as flow cytometry or fluorimetry.

Depending on the ability of the test compound to inhibit syncytia, a range of results is generally obtained, from no syncytia to syncytia formation with all the cells. The fewer syncytia formed in the assay the better the test compound is at inhibiting syncytia formation. The use of virus-free cells for screening of molecules with anti-syncytial activity provides an assay system that does not need laboratories designed for work with dangerous microorganisms. In addition, and most importantly, this assay system will specifically select only for inhibitors of syncytia (fusion between gp160 and CD4 or "unknown" receptor-bearing cells) without interference of other functional components of the whole HIV-1 virus.

The potency and specificity of the HIV-inhibitors can also be evaluated by combining the cells of the invention with different types of human cell partners such as human T helper cells, monocytes and macrophages, and EBV infected cells. The capability of this viral-free assay system, to screen the HIV inhibitors against only one HIV function (binding and syncytia formation), makes this system unique not only for screening of anti-syncytia inhibitors but analyzing and evaluating specificity of other HIV inhibitors such as protease, and reverse transcriptase. This system also allows rapid screening of different cell types for their capability to form syncytia with BJAB-gp160 cells (e.g. different CD4+ cell types, EBV transformed cells, other virally infected cells).

Further, as the initial step of the HIV-1 infection of a cell is the binding and fusion of the envelope glycoprotein gp160 or vital particle with the CD4 receptor, the inhibition of this function becomes attractive for screening of inhibitors with anti-syncytia activity.

The cells of the invention are also expected to be useful as a vaccine. By presenting HIV gp160 envelope proteins to the immune system in a cell-associated form, as a part of the human lymphoid cell, the cells of the invention mimic HIV-1 infected cells in vivo. Because the cells of the invention express only one component of the virus, there is no danger that a person inoculated with the cells would be infected with the AIDS virus. BJAB cells expressing cell-surface gp160 would act as an immunogen to trigger an immunological mechanism of the host that may lead to the production of broadly protective and neutralizing antibodies and the generation of immune cells that may recognize and kill virus-infected cells and also prevent HIV dissemination. The cells of the invention present the immune system with fully functional and membrane-associated gp160 (gp120 and gp41) HIV-envelope proteins which can generate a unique repertoire of protective and neutralizing antibodies. The cellular form of HIV gp160 immunogen (gp120 and gp41) is expected to trigger cell-mediated immune responses which may play a key role in defense mechanism against HIV infection. Furthermore, the BJAB cell line is an immature B cell line that should elicit fewer unwanted antibodies or cross-reactions to surface proteins than more differentiated cells. Additionally, recombinant vaccine, such as the cells of the invention, can distinguish between a vaccine-induced seroconversion (antibody response only to gp160 protein) and naturally acquired HIV infection (antibodies against other HIV antigens).

The cells of the invention would also act as an adjuvant with respect to the presentation of gp160 to the immune system. In general, subunit vaccines are formulated in the base of an appropriate adjuvant in order to trigger the immune system. However, the cells of the invention are large enough to trigger the immune system themselves and thus could serve as the adjuvant. For such in vivo presentation, the cells would be irradiated or fixed according to standard techniques for the preparation of vaccines.

The cells of the invention can also serve as a model system for the generation of recombinant cell-based vaccines not only against HIV but also other viral diseases. Proteins from other viruses can be substituted for gp160 to provide vaccines for these viruses.

The cells of the invention represent a novel vaccine approach in which HIV-1 envelope proteins are presented to the immune system in cellular form, thereby having the potential to elicit humoral and cell-mediated immunity that are different from that elicited by the soluble antigen. Since gp160 is expressed on the cell surface in processed form (gp41 and gp120) and is therefore functional (syncytia formation), such system closely mimics HIV-infected cells.

When used as a vaccine, the cells of the invention may be administered to a human patient prophylactically to prevent or inhibit infection of the person with HIV-1. The cells of the invention may also be administered as membrane preparations, fixed cells, or disrupted cells. Membrane preparations, fixed cells, and disrupted cells may be prepared by standard techniques such as sonication for preparation of disrupted cells. The cells are preferably administered in combination with a pharmaceutically acceptable carrier or diluent, such as a buffer or saline. Stabilizers, adjuvants and other compositions such as preservatives may also be added. The cells may be administered to a person according to conventional protocols for the administration of vaccines. The amount of vaccine administered in any particular case will depend on such factors as the age, sex, and weight of the individual. The vaccine may be administered by any effective route, including intramuscular and intravenous.

Because of the similarities between HIV-1 isolates and between human immunodeficiency virus-2 (HIV-2), it is expected that nucleotide sequences coding for gp160 from HIV-2 and from HIV-1 isolates other than BH-10 such as MN, RF, BaL and clinical isolates from persons infected with the virus can also be used for transfection of cells as described herein for HIV-1, and that the resulting cells expressing gp-160 from other isolates of HIV-1 or from HIV-2 will also be useful as vaccines and for syncytia formation assays, and for any other purpose for which cells expressing HIV-1 gp160 are useful.

Example 1

Preparation of BJAB Cells Expressing HIV-1 gp160 Construction of CLDN-gp160 plasmid The HIV-1 gp160 coding sequence was isolated on an MstII-XhoI 2945-base pair (bp) restriction endonuclease fragment from the BH10 HIV-1 viral isolate described by Shaw et al. (1984) Science 226: 1165–1171. This restriction endonuclease fragment carries the intact HIV-1 gp160 env gene as well as the two intact rev exons (coordinates 5535 to 8480, according to the numbering of Ratner et al (1985) Nature 313: 277), the disclosures of which are incorporated by reference as if fully set forth herein. The DNA sequence coding for HIV-1 gp160 used in the preferred embodiment is set out in FIG. 1 which shows the sequence of the MstII-XhoI restriction from BH10 carrying the full-length gp160 envelope gene and the two intact exons of the rev regulatory protein. The position of the gp120, gp41 and rev coding sequences is shown. The position of the XbaI linkers at each end of the restriction fragment is shown by an asterisk (*). The HIV-1 restriction fragment sequence shown is taken from sequence of HIV-1 disclosed in Ratner et al. supra.

After ligation to XbaI linkers and digestion with XbaI, this env-carrying fragment was inserted downstream of the cytomegalovirus (CMV) promoter in the CLDN expression vector. CLDN is a vector derived from pUC 19 which contains an SV40 origin of replication and three independent transcriptions cassettes for stable integration, high expression level, and amplification in a variety of mammalian cells. The first transcriptional cassette consists of the strong and constitutive cytomegalovirus (CMV) immediate early (IE) promoter isolated on an Spe1-Sac1 restriction endonuclease fragment from the CDM8 vector described by Seed (1987) Nature 329: 840–842, a unique polylinker region (including an XbaI site) for insertion of genes and the bovine growth hormone (BGH) polyadenylation region (Pfarr, D. et al. (1986) DNA 5: 115–122). Downstream of the expression cassette are two dominant selectable markers. First is the mouse dihydrofolate reductase (DHFR) gene cassette which is used for methotrexate MTX selection and amplification (Subramani, S. et al. (1981) Mol. and Cell. Biol. 1: 854–864). Second, downstream from the DHFR cassette, is the bacterial neomycin resistance (NEO) cassette which is used for neomycin G418 selection (Colbere-Garapin, F. et al. (1981) J. Mol. Bio. 150: 1–14).

BJAB cells

BJAB cells are human cells (human Burkitt's lymphoma cell line) which are EBV (Epstein-Bart Virus) and EBNA (EBV nuclear antigen) negative. BJAB cells were obtained from Dr. Henle, Children's Hospital of Pennsylvania, Philadelphia, Penn. The cells are Epstein-Barr virus and Mycoplasma free. Cells grow in suspension, and have doubling time of approximately 15 hours. The karyotype of BJAB cells is stable after transfection. BJAB cells were cultured in TY medium supplemented with 15% fetal calf serum (FCS) at 37 C in a 7% $CO_2$ atmosphere.

Transfection and expression of gp160

BJAB cells were transfected with CLDN-gp160 plasmid DNA by electroporation and clones selected for neomycin resistance. Selected clones were screened for expression of gp160 with a panel of antibodies (monoclonal and polyclonal) by immunocytochemistry and by their capability to form syncytia with human lymphoid cells of CD4+ phenotype.

The following media and solution were used in the transfection and selection of clones expressing gp160.

1) HY Medium—To 500 ml of DMEM-HB (Dulbecco's Modified Eagle—high glucose medium with 10% fetal calf serum (FCS) add: 5 ml of L-glutamine (100X) [200 mM], 5 ml of oxaloacetate, pyruvate, insulin (OPI)(100X) (to prepare 100 ml of 100X OPI combine: CIS-oxalic acid, 1500 mg, Sigma D-7753, insulin, 2000 U, SIGMA I-6634; pyruvic acid, 500 mg. Sigma P-5280), 5 ml hypoxanthine, thymidine (HT)(100X, Gibco 32D-1067 (to prepare 100 ml of 100X HT, combine: hypoxanthine $10^{-2}$M thymidine $1.6 \times 10^{-3}$M), 0.5 ml gentamicin (10 mg/ml, Gibco #600-5710), (HY-medium - Gibco).

2) TY Medium[19]—To 500 ml of HY medium with 15% FCS add: 0.5 ml ITS [insulin, transferrin, selenium (CR-ITS Premix, Collaborative Research)], 2 µl 2-aminoethanol (Sigma ED135), 2 µl 2-mercaptoethanol (Sigma Chemical Co., St. Louis, Miss.), Electroporation was done using a BTX Electro Cell Manipulator, Model 401-AM (BTX, Biotechnologies - Experimental Research, Inc., 3742 Lawell Street, San Diego, Calif., U.S.A.). The chambers used for electroporation were Flat chamber 481 (0.5 ml volume/1.0 mw gap). Electroporation was monitored using an optimizer (BTX Optimizor 50) with graphic pulse analyzer. For BJAB cells suspended in phosphate buffered saline (PBS), optimal conditions were an amplitude of 500–999 (2.4 kV/cm–4.2 kV/cm) and a pulse width of 99 µsec. At an amplitude of 999 and pulse width of 99 µsec, viability of human BJAB cells was 85% in PBS.

BJAB cells were grown in HY medium with 15% FCS. The cells were split and refed the day before electroporation. Prior to electroporation, cells were washed twice with ice-cold PBS pH 7.0, and resuspended in ice-cold PBS at $10^7$ cells/ml (this ensures 95% cell viability). Prior to use, plasmid DNA was ethanol precipitated and resuspended in sterile PBS. 10–50 µg of plasmid DNA (supercoiled or linearized plasmid) per $5 \times 10^6$ cells is added to the cell suspension, mixed well, incubated for 10 minutes on ice, and then this mixture is placed into the electroporation chamber. The electroporation chamber, previously stored in 70% ethanol was washed thoroughly with cold PBS, placed on ice and connected to the electrocell manipulator. 0.5 ml of the BJAB-DNA mixture was added to the chamber. The cells received single/multiple pulses under at the conditions described above. Under these conditions approximately 75% cells were viable after one hour at 37° C. The electroporated cells were transferred into a tube and kept on ice for ten minutes. TY medium was added to the cells and the cells were transferred to culture dishes. Medium was replaced weekly.

For selection of clones expressing gp160, a selection medium containing TY medium supplemented with 800 µg/ml G418 (Geneticin, G418 sulphate, Gibco) was used, and clones were selected according to the method in Harlow et al., *Antibodies, A Laboratory Manual*, Cold Spring Harbor Laboratories, Cold Spring Harbor, N.Y.

BJAB cells incubated with either plasmid DNA alone or calcium phosphate failed to be transfected with the plasmid DNA and did not form proliferating colonies.

Clone TF228.1 showed the highest expression levels of gp160 per cell and uniformity of gp160 expression with respect to total cell population expressing the gene. To assure monoclonality, cells were cloned by limited dilution and were screened for function, expression and stability.

Characterization of TF228.1

Indirect immunofluorescence immunocytochemistry to test anti-gp120, anti-gp41 and soluble T4 (sT4) binding was performed using standard techniques such as those described in Harlow et al., *Antibodies, A Laboratory Manual*, Cold Spring Harbor Laboratories, Cold Spring Harbor, N.Y. Pandex assay to test anti-gp120 and anti-gp41 binding was performed according to the method in "Whole-cell applications of PCFIA" in: Proceedings of the 1987 Pandex Symposium on Particle Concentration Fluorescence Immunoassay (Baxter Corporation, Chicago, Ill.). Western blot analysis was performed using standard techniques such as those described in Harlow et al., *Antibodies, A Laboratory Manual*, Cold Spring Harbor Laboratories, Cold Spring Harbor, N.Y.

As indicated in Table I, several assay systems showed that gp120 is expressed on the surface of BJAB cells. Several different antibodies indicated positive binding to gp120 and gp41 molecules. The binding of soluble CD4 (sT4) to gp160 indicated that the gp120 portion of the molecule has appropriate conformational structure to bind the CD4 receptor.

TABLE I

| CHARACTERIZATION OF TF228.1 CLONE (HIV-gp160) | |
|---|---|
| Assay System: | TF228.1 |
| Immunocytochemistry | |
| Anti-gp120 binding | + |
| Anti-gp41 binding | + |
| sT4 binding | + |
| Pandex assay | |
| Anti-gp120 binding | + |
| Anti-gp41 binding | + |
| Western blot analyses | + |

Example 2

Syncytia formation $3.5 \times 10^4$ five to six day old cultures of SupT1 cells a (CD4+ human T lymphocytic line) and $1.75 \times 10^4$ five to six day old cultures of TF228.1.16 (gp160) cells in forty microliters of buffer per each cell type were placed in the same well of 96 well plates. No test compound was added to controls. Twenty microliters of test compound was added to the remaining wells. The cells were incubated for 16–18 hours at 37 C, 7.5% $CO_2$ to allow formation of syncytia. Syncytia were then counted under a microscope (Biostar) at 40×magnification. The number of syncytia formed in wells containing test compound is expressed as percentage reduction of syncytia formed in control wells. (i.e., the number of syncytia formed in wells containing test compound divided by the number of syncytia formed in control wells.)

As indicated in Table II, several human T cell lines and primary human lymphocytes showed syncytia formation with the TF228.1 clone. When compounds are tested for their ability to inhibit syncytia formation, they may be tested with one or several combinations of cells.

TABLE II

SYNCYTIA FORMATION
CD4 + Human T-Cells/Cell lines

|  | SUPT1 | MOLT4 | Primary human T lymphocytes | CD4⁻ human cell line TF112B3.1 (control) |
|---|---|---|---|---|
| HIV-gp160 BJAB Transfectant TF228.1 | + | + | + | − |

Example 3
Syncytia Formation Assay

Soluble CD4 (sT4), a soluble recombinant form of the CD4 receptor found on human lymphocytes, and Leu-3a anti-CD4 monoclonal antibodies (Becton Dickinson Immunocytochemistry Systems, San Jose, Calif.) were tested using the syncytia formation assay described in Example 2. 20 μl of Leu-3a or sT4 dilution were added to the cells after they were placed in the microtiter wells. Inhibition of syncytia formation was followed by counting the number of syncytia present and by [$^3$H] TdR uptake.

Increasing concentrations of sT4 increased the inhibition of syncytia formation by sT4. At a concentration of 10 μg/ml sT4 inhibited syncytia formation by 10 per cent when compared to controls. At a concentration of 50 μg/ml sT4 inhibited syncytia formation by about 25–35 per cent when compared to controls. Syncytia formation was inhibited by about 45–55 per cent when compared to controls when sT4 was present at a concentration of 100 μg/ml. At a concentration of 250 μg/ml sT4 inhibited syncytia formation by about 85 to 100 per cent when compared to controls. When sT4 was present in the medium at a concentration of 500 μg/ml syncytia formation was inhibited by 100 per cent when compared to controls.

Syncytia formation was also significantly inhibited when increasing concentrations of Leu-3a were added. When Leu-3a was present at a concentration of 2.4 ng/ml syncytia formation was inhibited by 20 per cent when compared to controls. Increasing Leu-3a concentrations up to 19.5 ng/ml resulted in similar inhibition of syncytia formation (about 5–15 per cent inhibition with 4.8 ng/ml; about 5–24 per cent inhibition with 9.7 ng/ml; and about 18–25 per cent inhibition with 19.5 ng/ml). At 39 ng/ml Leu-3a inhibition of syncytia formation increased dramatically to about 50–65 per cent inhibition when compared to controls. And at 78 ng/ml Leu-3a inhibition of syncytia formation was 100 per cent when compared to controls. Similarly, inhibition of syncytia formation at 156 ng/ml was 85–100 per cent.

Example 4

In vitro Stimulation/Activation of Human Lymphocytes With TF228.1.16 Cells

Peripheral blood mononuclear (PBM) cells were isolated from day old Red Cross blood on a ficoll-hypaque density gradient and cultured together with irradiated (3000R) TF228.1 cells at a ratio of 50:1 or 100:1 PBM to TF228.1 cells. The final cell density was 5×10$^6$ cells/ml. The cell mixtures were incubated at 37° C. in a 7% CO$_2$ atmosphere in TY media containing 25% mixed lymphocyte culture (MLC) supernatant and 5 U/ml interleukin-2 (IL2) (Boehringer-Mannheim Corporation, Indianapolis, Ind.) for either 6 or 10 days. (MLC supernatant was generated by mixing together the peripheral blood lymphocytes of two patients, incubating the cells for 8–10 days, and collecting the supernatant from the cells.) Culture supernatants containing human antibodies were obtained by low speed centrifugation at 1,500×g.

Culture supernatants (1X final concentration) were added to the syncytia assay described in Example 2 with the modification that TF228.1 cells were preincubated with the culture supernatants containing human antibodies thirty minutes prior to adding SupT-1 cells. Syncytia were counted after twenty hours of incubation. The results of the syncytia assay are shown in Table 3. Very small syncytia indicate partial inhibition of syncytia formation.

Specificity of human antibodies in the culture supernatants to HIV-gp120 was measured by ELISA using recombinant gp120 from a Drosophila cell line as antigen. Purified gp120 was bound to the wells of a 96-well microtiter plate by incubating at 4° C. for twenty four hours. After blocking with 1% BSA in PBS containing 0.02% NaN$_3$ for one hour, culture supernatants were added to the wells and incubated for two hours. Antibody to gp120 was detected using peroxidase labeled goat-anti-human IgG, IgM and o-phenylenediamine. Results are represented in Table 3 as optical density readings at 460 nm.

As shown in Table 3, after six days of in vitro immunization, the number of antibodies specific for gp120 was not significant at either cell ratio when compared to controls which did not contain culture supernatant and the number of syncytia counted was not significantly less than the number found in the controls. After ten days of in vitro immunization, the number of antibodies specific for gp120 was significantly higher at both cell ratios than the number found after six days and no syncytia formation could be detected. Thus TF228.1 cells expressing HIV-1 gp160 are effective in provoking antibodies that prevent syncytia formation in Vitro.

TABLE 3

In Vitro Immunization of human PBM with TF228.1 cells

| Days of In Vitro Immunization | Ratio PBM:TF228.1 | Number of Syncytia | ELISA (gp120 Drosophila) |
|---|---|---|---|
| Day 6 | 50:1 | 48$^1$ | 0.117 |
|  | 100:1 | 69$^1$ | 0.191 |
| Day 10 | 50:1 | 0 | 0.540 |
|  | 100:1 | 0 | 0.361 |
| Control 1 |  | 44$^2$ | 0.131 |
| Control 2 |  | 50$^2$ | 0.089 |

$^1$small syncytia
$^2$large syncytia

What is claimed is:

1. A CD4 negative, Epstein-Barr virus negative, human Burkittle lumphoma modified to stably express a heterologous protein consisting of the entire human immunodeficiency virus envelop protein gp160 and which is capable of forming syncytia with human lymphoid cells of CD4+ phenotype.

2. The cell of claim 1 wherein the human immunodeficiency virus is human immunodeficiency virus-1.

3. The cell of claim 1 wherein said cell is a BJAB cell.

4. The cell of claim 3 which is TF228.1.16.

* * * * *

UNITED STATES PATENT AND TRADEMARK OFFICE
CERTIFICATE OF CORRECTION

PATENT NO. : 5,462,872
DATED : October 31, 1995
INVENTOR(S) : Jonak, et al.

It is certified that error appears in the above-identified patent and that said Letters Patent is hereby corrected as shown below:

Column 12, line 54, change "Burkittle lumphoma" to -- Burkitt's lymphoma cell --.

Signed and Sealed this

Sixth Day of February, 1996

Attest:

BRUCE LEHMAN

*Attesting Officer*          *Commissioner of Patents and Trademarks*